United States Patent [19]

Beyar et al.

[11] Patent Number: 5,520,700
[45] Date of Patent: May 28, 1996

[54] STAPLER DEVICE PARTICULARLY USEFUL IN MEDICAL SUTURING

[75] Inventors: Mordechai Beyar, Caesarea; Amnon Foux, Haifa, both of Israel

[73] Assignee: Technion Research & Development Foundation, Ltd., Haifa, Israel

[21] Appl. No.: 150,517

[22] Filed: Nov. 10, 1993

[30] Foreign Application Priority Data

Nov. 13, 1992 [IL] Israel ............................................. 103737

[51] Int. Cl.⁶ .................................................... A61B 17/00
[52] U.S. Cl. .......................... 606/139; 606/232; 227/175.1
[58] Field of Search ................................... 606/213, 219, 606/220, 232, 215, 151, 148, 144, 139, 75, 99, 100; 227/902, 175, 176, 178, 179, 180, 181, 19; 604/60, 61

[56] References Cited

U.S. PATENT DOCUMENTS

| | | | |
|---|---|---|---|
| 870,021 | 11/1907 | Duffee | 606/113 |
| 2,655,921 | 10/1953 | Haboush | 606/100 |
| 3,388,847 | 8/1965 | Kasulin et al. . | |
| 3,551,987 | 1/1971 | Wilkinson | 227/19 |
| 3,593,903 | 7/1971 | Astafiev et al. . | |
| 4,422,567 | 12/1983 | Haynes . | |
| 4,576,167 | 3/1986 | Noiles | 227/179 |
| 4,664,305 | 5/1987 | Blake, III et al. . | |
| 4,898,156 | 2/1990 | Gatturna et al. . | |
| 4,899,743 | 2/1990 | Nicholson et al. . | |
| 4,946,468 | 8/1990 | Li . | |
| 4,968,315 | 11/1990 | Gatturna . | |
| 4,969,892 | 11/1990 | Burton et al. | 606/232 |
| 5,002,550 | 3/1991 | Li . | |
| 5,013,292 | 5/1991 | Lemay | 606/232 |
| 5,037,422 | 8/1991 | Hayhurst et al. . | |
| 5,057,112 | 10/1991 | Sherman et al. | 606/100 |
| 5,149,329 | 9/1992 | Richardson | 604/272 |
| 5,156,616 | 10/1992 | Meadows et al. . | |
| 5,203,787 | 4/1993 | Noblitt et al. | 606/232 |
| 5,207,679 | 5/1993 | Li . | |
| 5,217,486 | 6/1993 | Rice et al. | 606/232 |
| 5,222,508 | 6/1993 | Contarini . | |
| 5,224,946 | 7/1993 | Hayhurst et al. . | |
| 5,242,457 | 9/1993 | Akopov et al. | 606/220 |
| 5,328,077 | 8/1994 | Lou | 227/175 |

FOREIGN PATENT DOCUMENTS

| | | | |
|---|---|---|---|
| 0140557 | 5/1985 | European Pat. Off. . | |
| 0558993 | 9/1993 | European Pat. Off. . | |
| 1539593 | 10/1967 | France . | |
| WO88/02246 | 4/1988 | WIPO | 606/100 |
| 89/10096 | 11/1989 | WIPO . | |

Primary Examiner—Stephen C. Pellegrino
Assistant Examiner—Jeffrey A. Schmidt
Attorney, Agent, or Firm—Levisohn, Lerner, Berger & Langsam

[57] ABSTRACT

A stapler device includes a manually grippable handle containing a drive and a trigger to activate the drive mechanism, a barrel fixed to the handle, a guide for holding a staple to be ejected and formed to accommodate a suture thread fixed to the staple, and an ejector driven by the drive through the barrel for ejecting a staple out through the guide into a bone to enable the suture, so anchored to the bone, to be used for various medical operations.

27 Claims, 3 Drawing Sheets

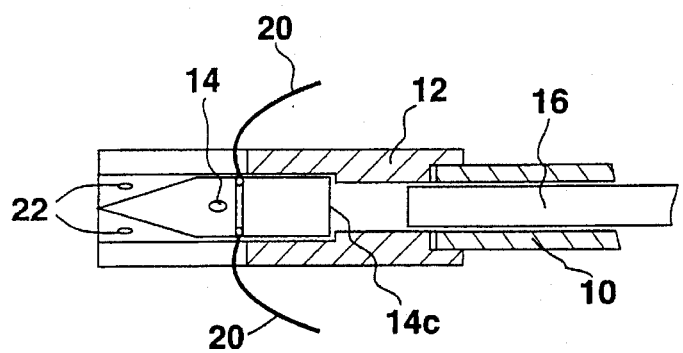
FIG. 4
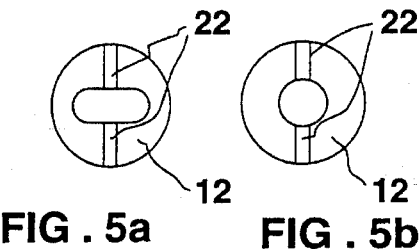
FIG. 5a   FIG. 5b
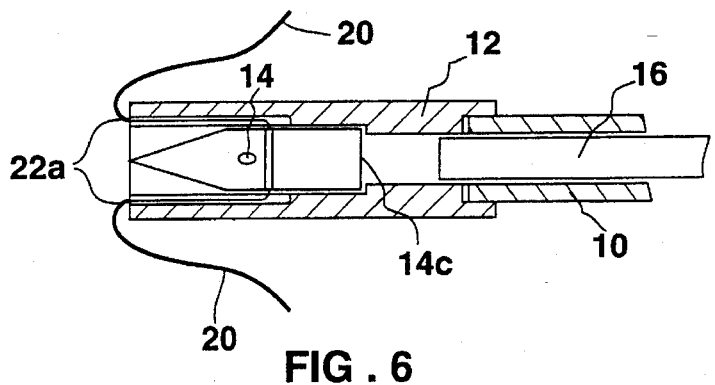
FIG. 6
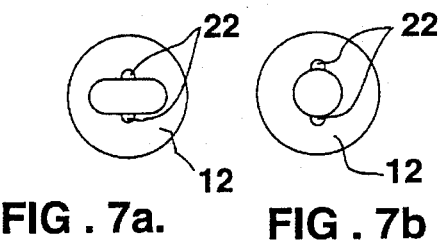
FIG. 7a.   FIG. 7b
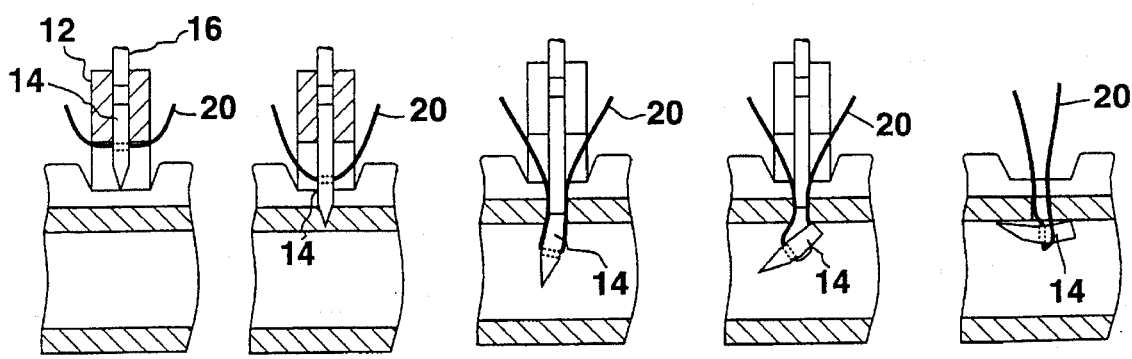
FIG. 8a   FIG. 8b   FIG. 8c   FIG. 8d   FIG. 8e

5,520,700

1

STAPLER DEVICE PARTICULARLY USEFUL IN MEDICAL SUTURING

FIELD AND BACKGROUND OF THE INVENTION

The present invention relates to a stapler device, and particularly to a stapler device useful in medical suturing. The invention is especially useful in treating urinary stress incontinence, and is described below with respect to such an application, but it will be appreciated that the invention could advantageously be used in other applications as well, such as in treating a recurrent shoulder dislocation condition.

Urinary stress incontinence, i.e., the inability to control urination from the bladder, is a distressing problem for more than ten percent of elderly women as well as for many young women. This condition frequently arises in the following manner: In a normally anatomically positioned bladder, the proximal urethra and the bladder are in pressure continuity with the abdominal cavity, so that an increase in abdominal pressure is transmitted both to the bladder and to the proximal urethra, resulting in normal continence. However, particularly among elderly women, the bladder and the proximal urethra tend to descend from their normal anatomic positions such that the bladder neck and proximal urethra move away from the posterior wall of the pubic bone. When this occurs, the proximal urethra is no longer in pressure continuity with the abdominal cavity; therefore, an increase in intra-abdominal pressure (e.g., by laughing or coughing) results in an increase in the intravesical pressure, but no change in the urethral closing pressure, thereby producing stress incontinence. It also appears that as the bladder descends, the urethra becomes shorter and curved, so that its radial tonic muscle contraction is reduced, contributing to incontinence.

Many treatments have been devised to correct stress incontinence. One treatment is by a surgical operation, involving an incision in the abdominal wall and/or interior vaginal wall, to return the bladder and proximal urethra to their normal anatomic positions by elevating them towards the posterior wall of the pubic bone in order to bring them into pressure continuity with the abdominal cavity. Another medical treatment involves a closed operation in which the bladder neck is elevated by suture threads passing, with the aid of long needles, from both sides of the urethra in the bladder neck to the inferior abdominal wall.

OBJECTS AND BRIEF SUBJECT OF THE INVENTION

An object of the present invention is to provide a stapler device which is particularly useful for fastening threaded staples to a bone for various medical purposes, particularly to treat urinary stress incontinence in the latter type of closed operation.

According to the present invention, there is provided a stapler device, comprising: a handle manually grippable by a user; a barrel having inner and outer ends, the barrel being fixed at its inner end to the handle; a guide for holding a staple to be ejected, the guide having an inner end fixed to the outer end of the barrel and having an outer end from which the staple is ejected; a power drive carried by the handle; a trigger carried by the handle and engageable by a finger of a user to activate the drive mechanism; and an ejector driven by the drive through the barrel for ejecting a staple out through the outer end of the guide. The outer end of the guide is formed with a bore to receive a staple, and an axially-extending recess communicating with the bore to accommodate a suture thread fixed to the staple.

In one described embodiment, the barrel is rigid for holding the guide in a fixed prescribed direction; and in a second described embodiment, it is flexible to allow pointing of the guide in a desired direction.

In a third described embodiment, the end of the guide is formed with a slot, or a pair of slots, for receiving the thread fixed to the staple; and in a fourth described embodiment, it is formed with a groove, or a pair of grooves, for receiving the thread fixed to the staple.

Such a stapler device is particularly useful for treating women suffering from urinary stress incontinence caused by the descending of the bladder and the proximal urethra from their normal anatomical positions. Thus, the staple may be ejected through the vaginal wall to enter the pubic bone, and the suture thread secured to the staple may be used for attaching the bladder neck and the proximal urethra to the posterior wall of the pubic bone. Such a stapler device may also be used in other applications, for example in medical operations for the fixation of a shoulder capsule in a person suffering from chronic shoulder dislocation.

The invention also provides a staple including a suture thread secured thereto for ejection by the above-described novel stapler device.

Further features and advantages of the invention will be apparent from the description below.

BRIEF DESCRIPTION OF THE DRAWINGS

The invention is herein described, by way of example only, with reference to the accompanying drawings, wherein:

FIG. 4 is an enlarged sectional view of the staple guide in the stapler device of FIG. 1;

FIG. 5a is an end view illustrating the staple guide of FIG. 4; FIG. 5b is similar to FIG. 5a, illustrating a modification in the construction of the staple guide;

FIGS. 6 and 7a, 7b are views similar to FIGS. 4 and 5a, 5b, respectively, illustrating a modification in the construction of the staple guide;

FIGS. 8a–8e illustrate various stages in applying the staple and thread of FIGS. 2 and 3 to the pubic bone when treating for urinary stress incontinence (or other bone when treating for other conditions);

DESCRIPTION OF PREFERRED EMBODIMENTS

Figure 1:
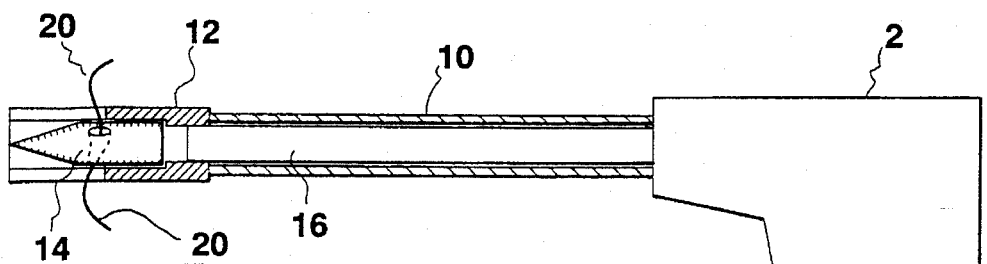
FIG. 1 illustrates one form of stapler device constructed in accordance with the present invention.

The stapler device illustrated in FIG. 1 comprises a housing, generally designated 2, including a handle 4 which is manually grippable by the user. The illustrated stapler device is pneumatically powered and therefore includes a connector 6 at the bottom of the handle 4 for attaching thereto a tube 8 connectible to a source of pressurized air. Housing 2 further includes an elongated barrel 10 having a staple guide 12 at its end for the staple 14 to be ejected. Ejection of the staple 14 is effected by an ejector pin 16 which is driven into sharp impact against the base of the staple 14 by the air pressure supplied from the pressurized air tube 8. Handle 4 includes a trigger 18 which, when depressed, applies an air pressure pulse to ejector pin 16 to cause it to impact against the base of staple 14 and thereby to eject the staple out through the end of guide 12. Insofar as described, such staple devices are known, and therefore further details of its construction and operation are not set forth.

As distinguished from the known constructions, the staple 14 ejected from the guide 12 at the end of barrel 10 in FIG. 1 has a suture thread 20 secured to the staple and ejected with it. In the above-described application, the staple is driven into the patient's pubic bone, and the thread 20 may then be used for fixing the bladder neck and proximal urethra thereto.

The staple 14 in FIG. 1 is made of elastic material. The staple is preferably shaped into the curved form illustrated at 14' in FIG. 2 while it is in its normal condition, and is deformed into the straight form shown at 14" in FIG. 3 while in a stressed condition. It is loaded into the stapler and ejected therefrom while in its straight stressed condition. After it has been so ejected, it returns to its curved form shown at 14' in FIG. 2, thereby better fixing the staple to the bone tissue it penetrated when ejected from the staple guide 12.

Figure 2:
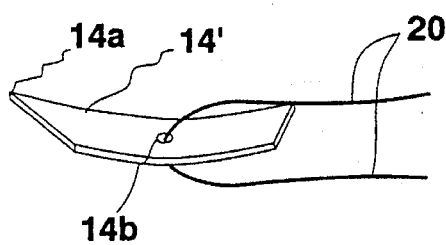
FIGS. 2 and 3 illustrate the natural curved shape and the temporary straight shape respectively, of one form of staple with attached thread in accordance with the present invention.
Figure 3:
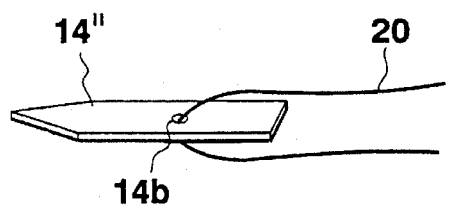

As shown in FIGS. 2 and 3, the staple 14 is formed with a pointed end 14a to enable it to penetrate the bone, and with a hole 14b approximately midway of its length for receiving the thread 20, similar to the manner in which a thread is received in the eye of a needle.

FIGS. 4 and 5a more particularly illustrate the staple guide 12 from which the staple 14, including its attached thread 20, is ejected. As shown, the outer end of this guide is formed with a bore for receiving the staple, and a pair of axially-extending recesses, in the form of slots 22, communicating with the bore to accommodate the thread 20. Thus, when the base 14c of staple 14 is impacted by the ejector pin 16, the thread 20 moves through slot 22, thereby permitting the staple guide 12 to snugly fit around the ejected staple 14.

FIGS. 6 and 7a illustrate a modification in the construction of the staple guide 12 in order to accommodate the thread 20 secured to the staple 14. In the modification of FIGS. 6 and 7a, the inner surface of the staple guide 12 is formed with a pair of grooves 22a serving as the recesses for accommodating the two sides of the thread 20.

FIGS. 5a and 7a show the bore in the outer end of the guide 12 for receiving the staple as being of oblong cross-section, to accommodate staples of oblong cross-section. The staples, however, may be of substantially circular cross-section, in which case the bores would also be of circular cross-section as shown in FIGS. 5b and 7b, respectively.

The manner of using the illustrated stapler device will now be described particularly with reference to FIGS. 8a–8e.

Thus, the staple 14, together with its attached thread 20, is loaded into the staple guide 12 while the staple is in its straight condition as illustrated at 14" in FIG. 3. Depressing trigger 18 causes a high-pressure pulse of air to be applied to ejector pin 16. This pulse causes ejector pin 16 to impact against the end face 14c of the staple 14, thereby driving the staple into the bone as shown in FIGS. 8a and 8b. As soon as the staple penetrates the bone, it starts to return to its normal, curved shape as shown in FIGS. 8c and 8d. The staple is thus firmly anchored to the bone with its attached thread 20 extending through the opening formed by the staple through the bone, as shown in FIG. 8e.

Following is one procedure for performing the above-described operation: A 20F urethral catheter is inserted into the bladder, and a balloon is inflated to 20 cc and retracted gently downwardly against the bladder neck. The surgeon inserts two fingers into the vagina, pressing the interior vaginal wall with one finger on each side of the urethra, which is felt because of the inserted catheter. By pressing the fingers upwardly and backwardly, the bladder neck and proximal urethra are pressed against the posterior wall of the pubic bone. At this stage, two staples are ejected longitudinally on each side of the urethra, about 1–2 cm apart. The two threads on each side of the urethra are tied one to the the other. They may be tied on the vaginal mucosa, in which case the tension will embed the threads to the sub-mucosa after some time. Alternatively, the threads may be tied under the vaginal mucosa by passing one of the threads on the same side. The threads may be made of a monofilament non-absorbent material, as well as of an absorbent material, dependent on the preference of the physician.

In cases where the urethra itself is very wide, the threads may be used for engaging and elevating the urethra to the posterior pubic bone as in a "sling operation".

Figure 9:
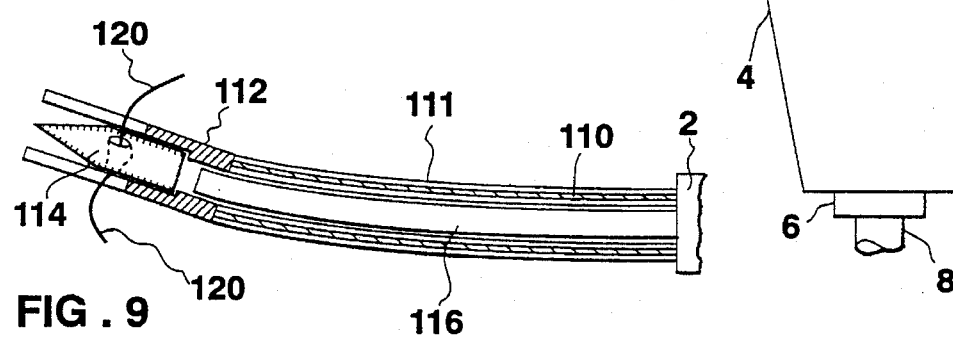
FIGS. 9–11 illustrate modifications in the construction of the stapler device of FIG. 1.
Figure 10:
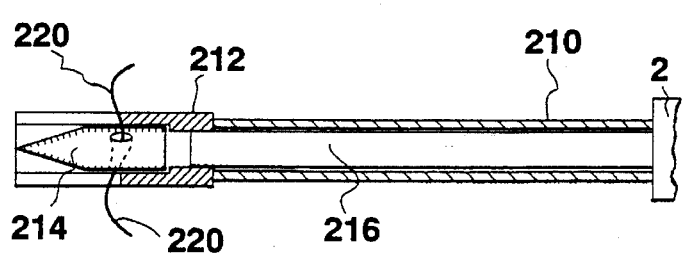

The stapler barrel 10 in FIG. 1 is preferably of a flexible plastic tube. FIG. 9 illustrates a variation wherein the stapler barrel is in the form of a closed helical wire 110 enclosed within a thin flexible tube 111, which increases the flexibility of the barrel and thereby facilitates its placement at the proper direction. FIG. 10 illustrates a variation wherein the barrel, therein designated 210, is a stiff or rigid tube.

Figure 11:
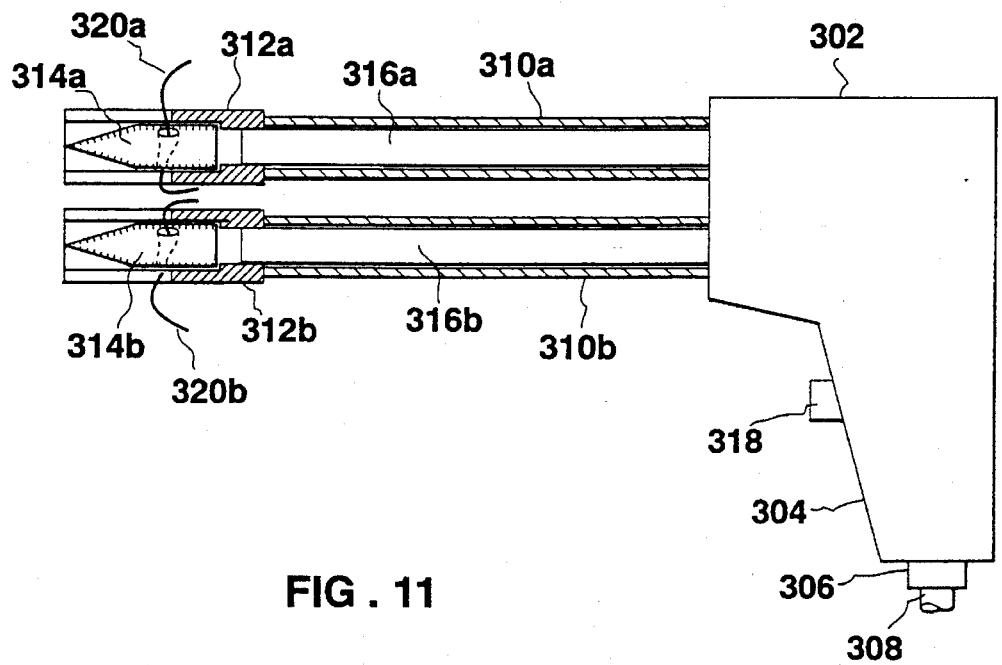

FIG. 11 illustrates a further variation wherein the stapler, therein designated 302, includes two barrels 310a, 310b in parallel relation to each other to enable two staples with attached threads to be ejected at the same time. In the modification illustrated in FIG. 11, each of the staple guides 321a, 312b receives a staple-thread unit 314a, 314b ejected by an ejector pin 316a, 316b received in the respective barrel, and both ejector pins are driven at the same time by high pressure pulses produced upon depression of the trigger 318.

FIGS. 12–18 illustrate other constructions of staple-thread units which may be used.

Figure 12:
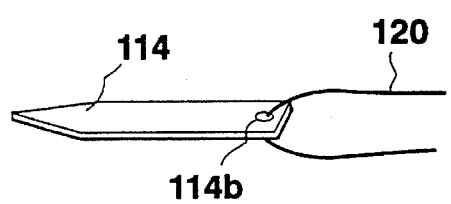
FIGS. 12–18 illustrate other forms of staple-thread units which may be used.

The unit illustrated in FIG. 12 includes a staple 114 and a thread 120 similar to the construction illustrated in FIGS. 2 and 3, except that the hole 114b through which the thread 120 is passed is at the rear end of the staple, rather than at the middle.

Figure 13:
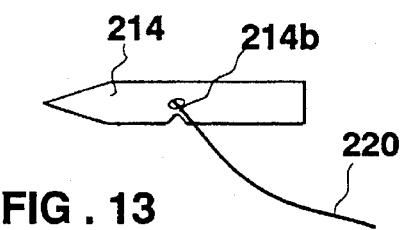
Figure 14:
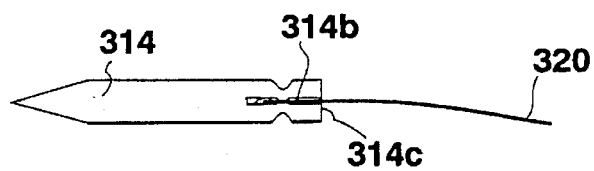
Figure 15:
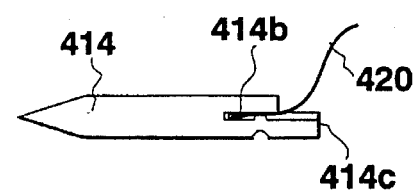

FIG. 13 illustrates a construction wherein the staple 214 is provided with a bore 214b extending at an angle to the longitudinal axis of the staple 214 with the end of the thread 220 received and fixed therein by crimping the staple. FIG. 14 illustrates a construction wherein the bore 314b is in the base 314c of staple 314 and extends along or parallel to the longitudinal axis of the staple 314, the thread 320 being received within the bore 314b and fixed therein by crimping the staple. FIG. 15 illustrates a construction similar to that of FIG. 14, except that part of the base 414c of the staple 414, formed with the axial bore 414b for receiving the thread 420, is cut away so that the impact of the ejector pin against the base of the staple will not impact against the end of the thread.

Figure 16:
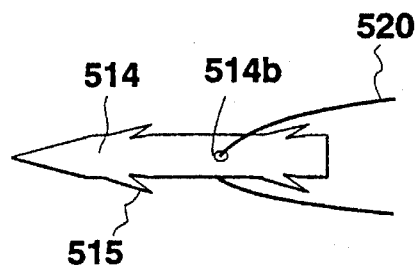

FIG. 16 illustrates a further variation wherein the staple 514 is formed with a plurality of barbs 515 projecting from its outer surface, to fix the staple to the bone which it penetrates. The thread 520 is passed through a hole 514*b* in the staple.

Figure 17:
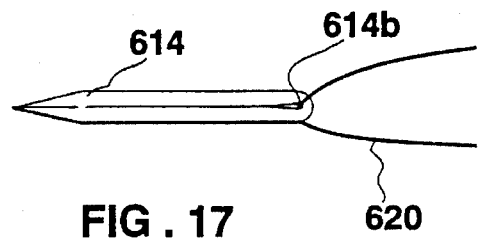
Figure 18:
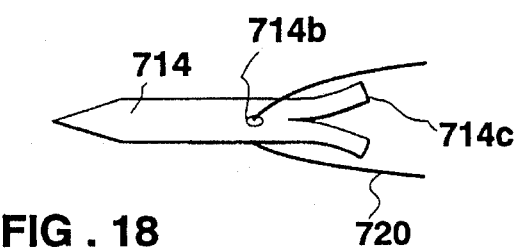

FIG. 17 illustrates a staple 614 made of bent wire with the thread 620 passing through a loop 614*b* in the bent wire. FIG. 18 illustrates a staple 714 with a split tail 714*c*, which is straightened when inserted into the staple guide 12. The thread 720 passes through a hole 714*b* in the staple.

While the invention has been described with respect to one particular application, it will be appreciated that the described stapler device and stapler-thread units may be used for other applications, e.g., for shoulder dislocations, endoscopic operations, or the like. The stapler may also be electrically operated and may use other mechanical impact devices for driving the stapler. The staples themselves may be of known bio-absorbable materials.

Many other variations and applications of the invention will be apparent.

What is claimed is:

1. A device for implanting a self-tapping staple having attached suture thread into the bone of a patient comprising:

a handle;

a barrel having a proximal end and a distal end, said proximal end being secured to said handle;

a staple guide for holding a staple, said staple guide being secured to said distal end of said barrel, the outer end of said staple guide being formed with a bore and a recess, said bore receiving a staple and said recess in communication with said bore physically accommodating the suture thread;

a power drive means for generating staple-ejecting and driving force into a bone, said force being sufficient to completely implant the staple into the bone and under the surface of the bone of a patient without predrilling a hole in the bone;

an ejector pin in communication with said power drive means and transmitting said force from said power drive means to the staple held in said staple guide; and, a trigger connected to said power drive means.

2. A device as claimed in claim 1, wherein said ejector pin is initially spaced from the staple immediately prior to activation of said trigger and constantly contacts the staple during ejecting and implanting the staple into the bone after activation of said trigger.

3. A device as claimed in claim 1, wherein said ejector pin has a from end for contact with the staple and said ejector pin contacts the staple without said front end coming into contact with the suture thread.

4. A device as claimed in claim 1, wherein said power drive means is pneumatic.

5. A device as claimed in claim 1, wherein said barrel is flexible.

6. A device as claimed in claim 1, wherein said recess comprises an axially extending slot.

7. A device as claimed in claim 1, wherein said recess comprises a pair of opposed axially extending slots for receiving a section of the suture thread.

8. A device as claimed in claim 1, wherein said recess extends to the outside surface of said barrel.

9. A device as claimed in claim 1, wherein said staple guide is separable from said barrel.

10. A device as claimed in claim 1, wherein said device comprises two parallel barrels each having a staple guide, each of said barrels also having an ejector pin connected to said power drive.

11. A device as claimed in claim 10, wherein each of said ejector pins is activated by a separate trigger, said triggers activating said ejector pins.

12. A device as claimed in claim 11, wherein said triggers sequentially activate each of said ejector pins.

13. A device as claimed in claim 10, wherein said ejector pins are activated by a single trigger.

14. A device as claimed in claim 10, wherein said single trigger activates both of said ejector pins simultaneously.

15. A device as claimed in claim 1, wherein said device further comprises a staple having a suture thread secured thereto.

16. A device as claimed in claim 15, wherein said staple is formed from an elastic material which changes shape when no longer held by said staple guide.

17. A device as claimed in claim 1, wherein said force comprises a single pulse.

18. A method of treating a female patient for urinary stress incontinence, comprising: inserting a bone anchor comprising a suture thread secured thereto through the vaginal wall of the patient to enter the pubic bone, and using said suture thread for securing soft tissue of the peri-urethral area to the posterior wall of the pubic bone to thereby adjust the anatomic position of the bladder neck and the urethra of the patient.

19. A method as claimed in claim 18, wherein said soft tissue comprises the vaginal wall.

20. A method as claimed in claim 18, further comprising the steps of forming a hole in said public bone by said step of inserting said bone anchor.

21. A method as claimed in claim 18, wherein said bone anchor is provided with a leading tip and a trailing, driven end and a longitudinal axis extending between said tip and said driven end and wherein the step of inserting said bone anchor results in a change of shape of said longitudinal axis.

22. A method as claimed in claim 21, wherein the shape of said longitudinal axis is changed by the use of a bone anchor formed from elastic material.

23. A method as claimed in claim 18, further comprising the steps of changing the orientation of said bone anchor as said bone anchor is inserted into the bone.

24. A method as claimed in claim 23, wherein said orientation is changed by the use of a bone anchor formed from elastic material.

25. A method as claimed in claim 18, wherein at least two bone anchors inserted into the pubic bone, and said step of using said suture thread comprises tying the suture threads of separate bone anchors together to secure said soft tissue to the posterior wall of said pubic bone.

26. A method as claimed in claim 25, wherein four bone anchors are inserted into the pubic bone.

27. A method as claimed in claim 18, wherein said step of inserting comprises ejecting and implanting of said bone anchor.

\* \* \* \* \*